United States Patent [19]
Raeymaekers et al.

[11] Patent Number: 5,527,915
[45] Date of Patent: Jun. 18, 1996

[54] IMMUNOSTIMULATING 6-ARYL-5,6-DIHYDROIMIDAZO[2,1-BETA] THIAZOLE DERIVATIVES

[75] Inventors: Alfons H. M. Raeymaekers, Beerse; Leopold F. C. Roevens, Rijkevorsel; Willy J. C. Van Laerhoven; Jean Pierre F. Van Wauwe, both of Beerse, all of Belgium

[73] Assignee: Janssen Pharmaceutica N.V., Beerse, Belgium

[21] Appl. No.: 242,686

[22] Filed: May 13, 1994

Related U.S. Application Data

[60] Continuation of Ser. No. 5,709, Jan. 19, 1993, abandoned, which is a division of Ser. No. 810,221, Dec. 19, 1991, Pat. No. 5,212,192, which is a continuation-in-part of Ser. No. 539,178, Jun. 18, 1990, abandoned, which is a continuation-in-part of Ser. No. 440,842, Nov. 24, 1989, abandoned.

[51] Int. Cl.$^6$ .................................................. C07D 277/40
[52] U.S. Cl. .................................................. 548/194
[58] Field of Search ...................................... 548/194

[56] References Cited

U.S. PATENT DOCUMENTS

| | | | |
|---|---|---|---|
| 3,274,209 | 9/1966 | Raeumaekers et al. | 260/306.7 |
| 4,340,738 | 7/1982 | Sipido | 548/151 |
| 4,584,305 | 4/1986 | Brugmans et al. | 514/368 |
| 4,911,315 | 3/1990 | Yamamoto et al. | 548/154 |

FOREIGN PATENT DOCUMENTS

| | | |
|---|---|---|
| 49-06099 | 2/1974 | Japan. |
| 1109149 | 4/1968 | United Kingdom. |

OTHER PUBLICATIONS

Otterness et al., "Effect of Levamisole on the Mitosis of Murine Thymocytes in Culture", Immunopharmacology 1, 245–254 (1979).
Merluzzi et al., "*In vitro* stimulation of murine lymphoid cell cultures by levamisole", Clin. exp. Immunol., 22, 486–492 (1975).
Hammouda et al., *CA* ; 101: 211027f (1984).
Robert et al., *CA*; 97: 55735b, and *J. Heterocycl. Chem.*, 19, 343–348 (1982).
Brabander et al., "Levamisole and R 26390: in search for better insight and activity.", *Acta Antwerpiensia*, 1991, 8 (2), 37–46.
Van Wauwe et al., "Anti–CD3 stimulation of murine spleen cells: comitogenic effects of levamisole and R 26390", *International Journal of Immunopharmacology*, 1991, 13 (6), 764.
Sharma Ind. J. Chem. Sect B 24B, 553 (1985) abstract only.
Meakins, J. Chem Soc. Perkins Trans I 1989 p. 643.

*Primary Examiner*—Robert Gerstl
*Attorney, Agent, or Firm*—Charles J. Metz

[57] ABSTRACT

The present invention relates to novel 6-aryl-5,6-dihydroimidazo[2,1-b]thiazole derivatives having immunostimulating properties, which are useful for treating humans and warm-blooded animals suffering from disorders and/or diseases wherein the immune system is impaired or suppressed. Processes of preparing said novel compounds and compositions containing the same as active ingredient.

9 Claims, No Drawings

IMMUNOSTIMULATING 6-ARYL-5,6-DIHYDROIMIDAZO[2,1-BETA] THIAZOLE DERIVATIVES

CROSS-REFERENCE TO RELATED APPLICATIONS

This is a continuation of our application Ser. No. 08/005,709, filed Jan. 19, 1993 now abandoned, which was a division of application Ser. No. 08/810,221, filed Dec. 19, 1991, now U.S. Pat. No. 5,212,192, which in turn was a continuation-in-part of application Ser. No. 07/529,178, filed Jun. 18, 1990, now abandoned, which was a continuation-in-part of application Ser. No. 07/440,842, filed Nov. 24, 1989, now abandoned.

BACKGROUND OF THE INVENTION

In U.S. Pat. No. 3,274,209 there are described 6-aryl-2,3,5,6-tetrahydroimidazo[2,1-b]thiazole derivatives as anthelmintics. The use of 2,3,5,6-tetrahydro-6-phenylimidazo[2,1-b]thiazole in aiding the regression of neoplastic disease is described in U.S. Pat. No. 4,584,305. The immunostimulating properties of (S)-(−)-2,3,5,6-tetrahydro-6-phenylimidazo[2,1-b]thiazole, generically known as levamisole, were described in Immunopharmacology 1, 245–254 (1979), Clin. exp. Immunol., 22, 486–492 (1975) and the references cited therein. The compound 5,6-dihydro-3,5,6-triphenylimidazo[2,1-b]thiazole is described in Gazz. Chim. Ital., 114, 201–204 (1984) [CA; 101: 211027f] and the compound 5,6-dihydro-6-phenylimidazo[2,1-b]thiazole-3-acetic acid ethyl ester, dihydrochloride in J. Heterocycl. Chem., 19, 343–348 (1982). Neither compound appears to have any useful pharmacological or other properties.

The compounds of the present invention differ from the prior an by the fact that the 2,3-bond is unsaturated and that either the 2 and/or the 3-position are substituted. Further, the present compounds are unexpectedly far more potent immunostimulating drugs than the prior-art compound levamisole.

2-Hexyl-5,6-dihydro-6-phenylimidazo[2,1-b]thiazole oxalate has been described in Acta Antwerpiensia, 1991, 8 (2), 37–46 and in the International Journal of Immunopharmacology, 1991, 13 (6), 764.

DESCRIPTION OF THE INVENTION

The present invention is concerned with novel 6-aryl-5,6-dihydroimidazo[2,1-b]thiazole derivatives having the formula

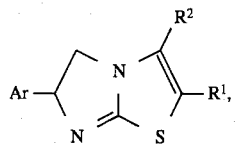 (I)

the pharmaceutically acceptable acid addition salts thereof and the stereochemically isomeric forms thereof, wherein Ar is phenyl optionally substituted with from 1 to 3 substituents each independently selected from halo, hydroxy, $C_{1-6}$alkyloxy, mercapto, $C_{1-6}$alkylthio, $C_{1-6}$alkyl, nitro, amino, mono- and di($C_{1-6}$alkyl)amino, $C_{1-6}$alkylcarbonylamino, arylcarbonylamino, $C_{1-6}$alkylsulfonylamino, trifluoromethyl, cyano, aminocarbonyl, mono- and di($C_{1-6}$)aminocarbonyl, hydroxycarbonyl, $C_{1-6}$alkyloxycarbonyl, carboxaldehyde and hydroxymethyl; pyridinyl; thienyl; furanyl or furanyl substituted with either $C_{1-6}$alkyl or halo;

$R^1$ and $R^2$ each independently are $C_{1-20}$alkyl, ($C_{3-7}$cycloalkyl)$C_{1-6}$alkyl, $C_{3-7}$cycloalkyl, aryl or (aryl)$C_{1-6}$alkyl; and one of $R^1$ and $R^2$ may also be hydrogen; or $R^1$ and $R^2$ taken together may also form a $C_{3-6}$alkanediyl radical; each aryl independently is phenyl optionally substituted with from 1 to 3 substituents each independently selected from halo, hydroxy, $C_{1-6}$alkyloxy, $C_{1-6}$alkyl, nitro, amino, trifluoromethyl or cyano.

In the foregoing definitions $C_{1-6}$alkyl defines straight and branch chained saturated hydrocarbon radicals having from 1 to 6 carbon atoms such as, for example, methyl, ethyl, propyl, 1-methylethyl, butyl, 1-methylpropyl, 2-methylpropyl, 1,1-dimethylethyl, pentyl, hexyl and the like; $C_{1-20}$alkyl defines $C_{1-6}$alkyl and the higher homologs thereof having from 7 to 20 carbon atoms such as, for example, heptyl, octyl, nonyl, decyl, undecyl, dodecyl, tridecyl, tetradecyl, pentadecyl, hexadecyl, heptadecyl, octadecyl, nonadecyl, eicosyl and the branched isomers thereof; $C_{3-7}$cycloalkyl defines cyclopropyl, cyclobutyl, cyclopentyl, cyclohexyl or cycloheptyl; $C_{3-6}$alkanediyl defines bivalent straight and branch chained hydrocarbon radicals having from 3 to 6 carbon atoms such as, for example, 1,3-propanediyl, 1,4-butanediyl, 1,5-pentanediyl, 1,6-hexanediyl and the like; halo defines fluoro, chloro, bromo and iodo.

A particular subgroup within the compounds of formula (I) as defined hereinabove comprises those compounds wherein $R^2$ is hydrogen.

Another particular subgroup comprises those compounds of formula (I) wherein $R^2$ is other than hydrogen.

Interesting compounds of formula (I) within the above defined subgroups are those compounds wherein Ar is phenyl optionally substituted with from one to two substituents independently selected from halo, nitro, hydroxy, $C_{1-6}$alkyloxy, $C_{1-6}$alkyl, $C_{1-6}$alkylcarbonylamino and arylcarbonylamino; thienyl; furanyl or pyridinyl.

Particularly interesting compounds are those interesting compounds wherein $R^1$ is $C_{4-10}$alkyl and Ar is phenyl optionally substituted with one halo, nitro, methoxy or methyl.

The most interesting compounds are 6-(4-bromophenyl)-2-hexyl-5,6-dihydroimidazo[2,1-b]thiazole; 6-(4-bromophenyl)-2-pentyl-5,6-dihydroimidazo[2,1-b]thiazole; 5,6-dihydro-2-pentyl-6-phenylimidazo[2,1-b]thiazole; 2-hexyl-5,6-dihydro-6-phenylimidazo[2,1-b]thiazole; 2-heptyl-5,6-dihydro-6-phenylimidazo[2,1-b]thiazole; and 5,6-dihydro-2-octyl-6-phenylimidazo[2,1-b]thiazole, the pharmaceutically acceptable acid addition salts thereof and the stereochemically isomeric forms thereof.

Preferred compounds are 2-hexyl-5,6-dihydro-6-phenylimidazo[2,1-b]thiazole; (S)-(−)-2-hexyl-5,6-dihydro-6-phenylimidazo[2,1-b]thiazole; (R)-(+)-2-hexyl-5,6-dihydro-6-phenylimidazo[2,1-b]thiazole; all mixtures of the latter enantiomeric forms as well as the pharmaceutically acceptable acid addition salts thereof.

Particular compounds of formula (I) are those, wherein $R^2$ is hydrogen or $C_{1-6}$alkyl; $R^1$ is $C_{1-18}$alkyl, ($C_{5-6}$cycloalkyl)methyl or $C_{5-6}$cycloalkyl, and in case $R^2$ represents $C_{1-6}$alkyl, then $R^1$ may also be hydrogen; and Ar is pyridinyl; thienyl; furanyl; or phenyl optionally substituted with one or two substituents each independently selected from halo, nitro, $C_{1-6}$alkyloxy or $C_{1-6}$alkyl.

More particular compounds are those particular compounds wherein $R^2$ is $C_{1-6}$alkyl; $R^1$ is hydrogen or $C_{1-4}$alkyl; and Ar is pyridinyl; thienyl; furanyl; or phenyl optionally substituted with halo, nitro, $C_{1-4}$alkyloxy or $C_{1-4}$alkyl.

Other more particular compounds are those particular compounds wherein $R^2$ is hydrogen; $R^1$ is $C_{3-10}$alkyl; and Ar is pyridinyl; thienyl; furanyl; or phenyl optionally substituted with halo, nitro, $C_{1-4}$alkyloxy or $C_{1-4}$alkyl.

Depending on the nature of the various substituents, the compounds of formula (I) may have several asymmetric carbon atoms. Unless otherwise mentioned or indicated, the chemical designation of compounds denotes the mixture of all possible stereochemically isomeric forms, said mixtures containing all diastereomers and enantiomers of the basic molecular structure. The absolute configuration of each chiral center may be indicated by the stereochemical descriptors R and S.

Stereochemically isomeric forms of the compounds of formula (I) are obviously intended to be embraced within the scope of the invention.

The compounds of formula (I) have basic properties and, consequently, they may be converted to their therapeutically active non-toxic acid addition salt forms by treatment with appropriate acids, such as, for example, inorganic acids, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanedicarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term pharmaceutically acceptable acid addition salts also comprises the solvates which the compounds of formula (I) may form and said solvates are intended to be included within the scope of the present invention. Examples of such solvates are e.g. the hydrates, alcoholates and the like.

The compounds of formula (I) can conveniently be prepared by cyclizing an intermediate of formula (II) in the presence of an appropriate activating reagent, optionally in a suitable reaction-inert solvent.

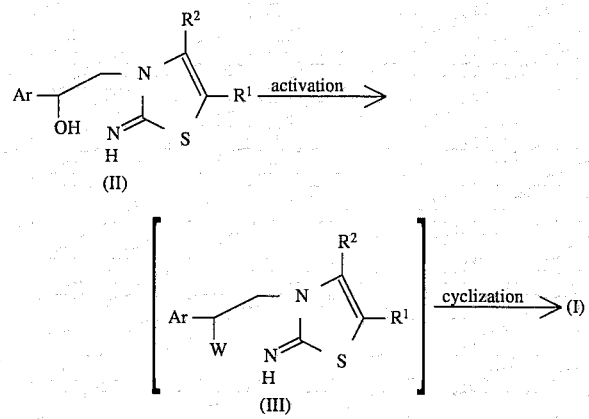

Appropriate activating reagents comprise reagents which can convert a hydroxygroup into a reactive leaving group W, such as, for example, inorganic and organic acids, e.g. hydrohalic acids, sulfuric acid, phosphoric acid, polyphosphoric acid, polyphosphoric acid ethyl ester, acetic acid and the like acids, halogenating reagents, e.g. thionyl chloride, phosphor trichloride, phosphoryl chloride, zinc chloride and the like halogenating reagents, sulfonylating reagents, e.g. methanesulfonyl chloride, methylbenzenesulfonyl chloride and the like, acylating reagents, e.g. acetic, propanoic and benzoic anhydride, acetyl, propionyl and benzoyl chloride, dehydrating reagents, e.g. dicyclohexylcarbodiimide and the like. Said leaving group W in the intermediate (III) represents, for example, hydroxonium, halo, e.g. chloro or bromo, an acyl group, e.g. acetyl, propionyl, benzoyl and the like or a sulfonyloxy group, e.g. methanesulfonyloxy, methylbenzenesulfonyloxy and the like groups. Suitable reaction-inert solvents are, for example, aromatic hydrocarbons, e.g. benzene, methylbenzene, dimethylbenzene and the like, halogenareal hydrocarbons, e.g. dichloromethane, trichloromethane, tetrachloromethane and the like, ethers, e.g. tetrahydrofuran, 1,1'-oxybisethane, 1,4-dioxane and the like, acetic anhydride and the like, or a mixture of such solvents. In some instances it may be appropriate to conduct the cyclization of the intermediate (III) in the presence of a base such as, for example, an alkali or earth alkaline metal carbonate or hydrogen carbonate such as, for example, sodium carbonate, potassium carbonate and the like or an organic base such as, for example, a tertiary amine, e.g. N,N-diethylethanamine, N,N-di(1-methylethyl)ethanamine, and the like. Said cyclization reaction can conveniently be conducted at room temperature, though it may be advantageous to heat the reaction mixture slightly in particular instances.

The compounds of formula (I) can also be prepared by reacting an imidazoline of formula (IV) or the equivalent tautomeric thiol form thereof, with a reagent of formula $R^1$—CH($W^1$)—C(=O)—$R^2$(V).

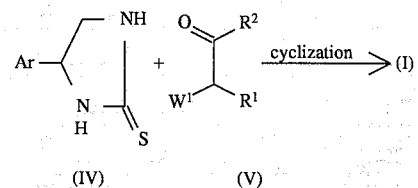

In formula (V) and hereinafter $W^1$ represents a reactive leaving group such as for example, halo, e.g. chloro or bromo, a sulfonyloxygroup, e.g. methanesulfonyloxy, benzenesulfonyloxy, 4-methylbenzenesulfonyloxy and the like. Said cyclization reaction may be carried out by stirring and, if desired, heating the reactants in a reaction-inert solvent, optionally in the presence of a suitable base. Appropriate solvents are, for example, alkanols, e.g. methanol, ethanol and the like, ketones, e.g. 2-propanone, 4-methyl-2-pentanone and the like, carboxylic acids, e.g. acetic, propanoic and the like acids, aromatic hydrocarbons, e.g. benzene, methylbenzene and the like, halogenated hydrocarbons, e.g. dichloromethane, trichloromethane, tetrachloromethane and the like, ethers, e.g. 1,1'-oxybisethane, tetrahydrofuran, 1,4-dioxane and the like, dipolar aprotic solvents, e.g. N,N-dimethylformamide, N,N-dimethylacetamide, pyridine and the like; or mixtures of such solvents. Suitable bases are, for example, inorganic bases, e.g. alkali or earth alkaline metal carbonates, hydrogen carbonates, oxides or hydroxides, e.g. sodium carbonate, sodium hydrogen carbonate, potassium carbonate, sodium hydroxide, potassium hydroxide and the like; sodium hydride; or organic bases such as, for example, alkali metal alkoxides, e.g. sodium methoxide, sodium ethoxide, potassium tert. butoxide and the like, amines, e.g. N-(1-methylethyl)-2-propanamine, N,N-diethylethanamine, 1,8-diazabicyclo[5,4,0]undec-7-ene and the like bases. In order to enhance the rate of the reaction it may be advantageous to heat the reaction mixture, more in particular to heat the reaction mixture at the reflux temperature.

In some instances it may be convenient to react the imidazoline (IV) with a protected derivative of the reagent of formula (V), in particular the acetal (VII), e.g. the dimethyl, diethyl, ethanediyl or propanediyl acetal, thus yielding an intermediate of formula (VI).

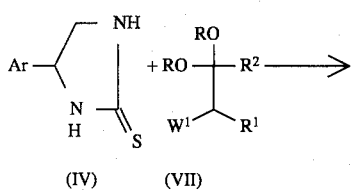

(IV)     (VII)

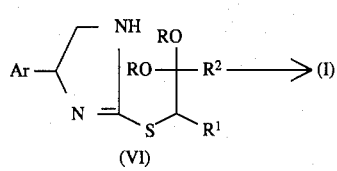

(VI)

Said intermediate (VI) may subsequently be cyclized to a compound of formula (I) by treatment with an appropriate acid such as, for example, hydrochloric acid, sulfuric acid and the like, a carboxylic acid, e.g. acetic, propanoic, trichloroacetic, trifluoroacetic and the like acids, in a suitable reaction inert solvent, as defined in the procedure hereinabove.

Some of the intermediates and starting materials in the foregoing are known and may be prepared according to art-known methodologies of preparing said or similar intermediates and starting materials, and a number of intermediates are novel. A number of such preparation methods will be described hereinafter in more detail.

The intermediates of formula (II) are novel and can generally be prepared from the intermediate ketones of formula (VIII) by reduction.

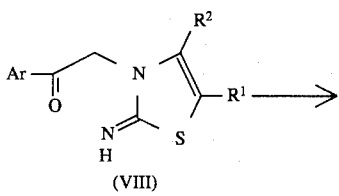

(VIII)

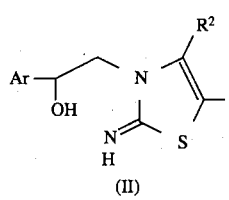

(II)

Said reduction can conveniently be earned out by treating the intermediate ketone (VIII) in an appropriate reaction-inert solvent with a reducing agent such as, for example, an alkali metal borohydride, e.g. lithium, potassium or, preferably, sodium borohydride, sodium cyanoborohydride, sodium tri(1-methylpropyl)borohydride, sodium triethylborohydride, sodium trimethoxyborohydride, sodium bis(2-methoxyethoxy)aluminum hydride, lithium aluminum hydride, lithium trialkoxyalanes and the like reducing reagents. Appropriate solvents are, for example, water, alkanols, e.g. methanol, ethanol, 1-propanol, 2-propanol and the like, ethers, e.g. 1,1'-oxybisethane, tetrahydrofuran, 1,4-dioxane, 2-methoxyethanol, 2,2'-oxybispropane, 1,2-dimethoxyethane, 1,1'-oxybis(2-methoxyethane) and the like, aromatic hydrocarbons, e.g. benzene, methylbenzene, dimethylbenzene and the like, or mixtures of such solvents.

Alternatively, the intermediates of formula (II) may also be obtained by reacting an epoxide of formula (IX) with a thiazolamine of formula (X).

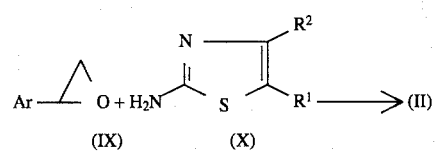

(IX)    (X)

Said reaction may conveniently be conducted by stirring and optionally heating the reactants in a reaction-inert solvent optionally in the presence of an appropriate acid. A suitable reaction-inert solvent is an aromatic hydrocarbon, e.g. benzene, methylbenzene and the like, a halogenated hydrocarbon, e.g. dichloromethane, trichloromethane, tetrachloromethane and the like; an ether, e.g. 1,1'-oxybisethane, tetrahydrofuran, 1,4-dioxane and the like, a dipolar aprotic solvent, e.g. N,N-dimethylformamide, N,N-dimethylacetamide, dimethylsulfoxide, acetonitrile and the like or a mixture of such solvents. Appropriate acids are organic acids like 4-methylbenzenesulfonic acid, methanesulfonic acid and the like.

The intermediates of formula (VIII) are also novel and can be obtained by N-alkylating a thiazolamine of formula (X) with a reagent of formula (XI) wherein W is a reactive leaving group as defined hereinabove.

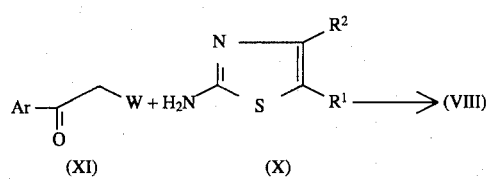

(XI)    (X)

Said N-alkylation reaction can be carried out by stirring and optionally heating the reactants in a reaction-inert solvent. As examples of reaction-inert solvents there may be mentioned alkanols, e.g. methanol, ethanol, 2-propanol, 1-butanol and the like; ketones, e.g. 2-propanone, 4-methyl-2-pentanone and the like; aromatic hydrocarbons, e.g. benzene, methylbenzene and the like, halogenated hydrocarbons, e.g. dichloromethane, trichloromethane, tetrachloromethane and the like; ethers, e.g. 1,1'-oxybisethane, tetrahydrofuran, 1,4-dioxane and the like, esters, e.g. ethyl acetate and the like, dipolar aprotic solvents, e.g. N,N-dimethylformamide, N,N-dimethylacetamide, dimethylsulfoxide, acetonitrile and the like or mixtures of such solvents. In some instances, the addition of an alkali metal iodide such as, for example, potassium iodide and the like may be appropriate.

The intermediates of formula (IV) can be obtained by cyclizing a diamine of formula (XII) with a reagent of formula L—C(=S)—L (XIII) wherein L represents an appropriate leaving group.

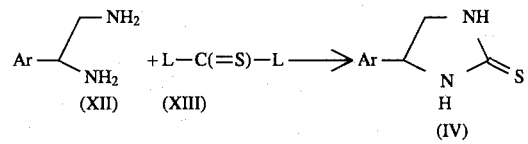

(XII)    (XIII)    (IV)

As typical examples of the reagents of formula (XIII) there may be mentioned thiourea, carbonothioic dichloride, carbon disulfide, 1,1'-carbonothioylbis[1H-imidazole] and the like reagents.

Said cyclization reaction may conveniently be conducted by stirring and optionally heating the reactants in a reaction-inert solvent such as, for example, an aromatic hydrocarbon, e.g. benzene, methylbenzene, dimethylbenzene and the like; a halogenated hydrocarbon, e.g. trichloromethane, tetrachloromethane, chlorobenzene and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, 1-methyl-2-pyrrolidinone, pyridine, methylpyridine, dimethylpyridine, tetrahydrothiophene 1,1-dioxide and the like; or a mixture of such solvents. In some instances however, it may be preferable to heat the reactants without a solvent. Further, it may be appropriate to add to the reaction mixture a base such as, for example, an amine, e.g. N,N-diethylethanamine, N-(1-methylethyl)-2-propanamine, 4-methylmorpholine and the like amines. When said reagent of formula (XIII) is carbon disulfide, the reaction may also be conducted conveniently in water or an alkanol such as, for example, methanol, ethanol, propanol and the like, in the presence of a base such as, for example, sodium hydroxide, potassium hydroxide and the like. Or alternatively, the latter reaction may also be conducted in a basic solvent such as, for example, pyridine and the like, in the presence of a phosphite such as, for example, diphenylphosphite.

The intermediates of formula (XII) generally can be prepared and resolved following the procedures described in Ann. Chem., 494, 143 (1932), incorporated hereinwith by reference. Alternatively, the diamines of formula (XII) may also be obtained by reacting an appropriately substituted aldehyde Ar-CHO with an alkali metal cyanide, e.g. sodium or potassium cyanide and the like, in the presence of ammonia or an acid addition salt form thereof such as ammonium hydrochloride and the like. The thus obtained aminonitrile may be reduced to a diamine (XII) following art-known reduction procedures such as, for example, catalytic hydrogenation with palladium-on-charcoal, platinum-on-charcoal, Raney nickel and the like, in a suitable solvent such as, for example, an alkanol, e.g. methanol, ethanol, 2-propanol and the like, an ether, e.g. 1,1'-oxybisethane, 2,2'-oxybispropane, tetrahydrofuran, 1,4-dioxane, an aromatic hydrocarbon, e.g. benzene, methylbenzene and the like, in the presence of a suitable acid such as, for example, hydrochloric acid, hydrobromic acid, acetic acid and the like.

The intermediates of formula (X) in turn can be obtained by reacting an intermediate of formula (V) with thiourea (XIV).

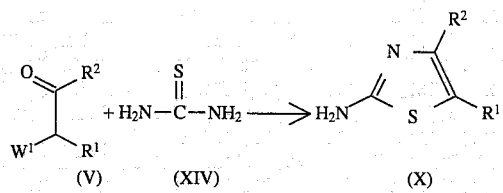

Said reaction can conveniently be conducted following the procedure described hereinabove for the preparation of the compounds of formula (I) from the intermediates (IV) and (V).

Alternatively, the intermediates of formula (X) may also be obtained by reacting intermediate (VII) with thiourea (XIV) and subsequently cyclizing the thus prepared intermediate (XV) with an appropriate acid as described hereinabove for the preparation of the compounds of formula (I) from intermediates (IV) and (VII).

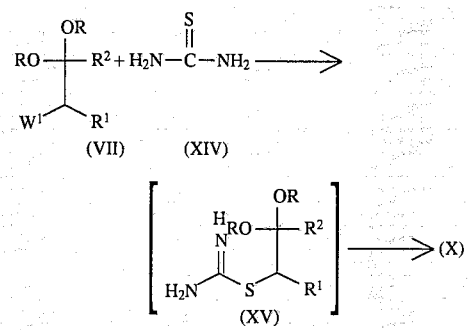

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, liquid chromatography and the like; and enantiomers may be separated from each other by the selective crystallization of their diastereomeric salts with optically active acids or preferably by chromatographic techniques, e.g. by liquid chromatography using a chiral stationary phase such as suitably derivatized cellulose, for example, tri(dimethylcarbamoyl)cellulose (Chiracel OD®) and the like. Pure stereochemically isomeric forms may also be derived from the corresponding pure stereochemically isomeric forms of the appropriate starting materials, provided that the reaction occurs stereospecifically.

Quite unexpectedly the present compounds are far more potent immunostimulating agents than the prior art compound (S)-(−)-2,3,5,6-tetrahydro-6-phenylimidazo[2,1-b]thiazole which is disclosed in U.S. Pat. Nos. 3,274,209 and 4,584,305 and is generically known as levamisole. The superior immunostimulating properties of the present compounds can clearly be demonstrated by measuring the increased $^3$H-thymidine incorporation in the presence of micromolar amounts of the present compounds, either in Concanavalin A-stimulated murine thymocytes or alternatively in anti-CD3-stimulated murine splenocytes. Whereas (S)-(−)-2,3,5,6-tetrahydro-6-phenylimidazo[2,1-b]thiazole (levamisole) displays its maximal costimulatory effect only at about 100 μM (Immunopharmacology 1, 246 (1979):

" . . . incorporation of $^3$H-thymidine is maximal in the concentration of range of 50 μg/ml (~200 μM))", the present compounds exhibit maximal costimulatory effects at concentration ranges from about 0.1 to about 1 μM. The present compounds are thus found to be active at concentration ranges a 100 to a 1000 times lower than that of the prior art compound.

Surprisingly, the novel intermediates of formula (II) and (VIII) too, have immunostimulating properties as can be demonstrated by the above described test procedures.

Consequently, the present invention is also concerned with intermediates of formula

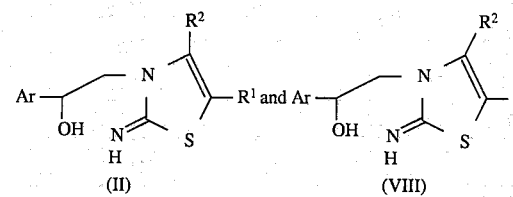

the pharmaceutically acceptable acid addition salts thereof and the stereochemically isomeric forms thereof wherein Ar, $R^1$ and $R^2$ are as defined under formula (I).

Particular intermediates of formula (II) and (VIII) are those, wherein $R^2$ is hydrogen or $C_{1-6}$alkyl; $R^1$ is $C_{1-18}$alkyl, ($C_{5-6}$cycloalkyl)methyl or $C_{5-6}$cycloalkyl, and in case $R^2$ represents $C_{1-6}$alkyl, then $R^1$ may also be hydrogen; and Ar is pyridinyl; thienyl; furanyl; or phenyl optionally substituted with one or two substituents each independently selected from halo, nitro, $C_{1-6}$alkyloxy or $C_{1-6}$alkyl.

More particular intermediates are those particular intermediates wherein $R^2$ is $C_{1-6}$alkyl; $R^1$ is hydrogen or $C_{1-4}$alkyl; and Ar is pyridinyl; thienyl; furanyl; or phenyl optionally substituted with halo, nitro, $C_{1-4}$alkyloxy or $C_{1-4}$alkyl.

Other more particular intermediates are those particular intermediates wherein $R^2$ is hydrogen; $R^1$ is $C_{3-10}$alkyl; and Ar is pyridinyl; thienyl; furanyl; or phenyl optionally substituted with halo, nitro, $C_{1-4}$alkyloxy or $C_{1-4}$alkyl.

In view of their improved immunostimulating properties, the compounds of formula (I) and the intermediates of formula (II) and (VIII) are taught to be useful in the treatment of humans and warm-blooded animals suffering from disorders and/or diseases wherein the immune system is impaired or suppressed. Typical examples of such disorders and/or diseases comprise, for example, bacterial infections, viral infections, e.g. verrucae, herpes simplex, vital hepatitis, AIDS and the like, tuberculosis, rheumatic disorders and the like. A particularly interesting use of the present compounds comprises their use as adjuvants in antineoplastic therapy. Said use may comprise treatment of the patient with a compound of formula (I) or an intermediate of formula (II) or (VIII) concomitant with antineoplastic therapy, as well as treatment of patients at risk of recurrent disease after having undergone antineoplastic therapy. The term antineoplastic therapy defines the methods commonly used to treat subjects suffering from malignant diseases such as, for example, surgery, radiotherapy and in particular chemotherapy.

In view of their useful pharmacological properties, the subject compounds and intermediates may be formulated into various pharmaceutical forms for administration purposes. To prepare the pharmaceutical compositions of this invention, an effective amount of the particular compound or intermediate, in acid addition salt or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carders are obviously employed. For parenteral compositions, the carder will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) and the intermediates (II) and (VIII) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carder. Examples of such dosage unit forms are tablets (including scored or coated tablets), capsules, pills, powder packets, wafers, injectable solutions or suspensions, teaspoonfuls, tablespoon fuls and the like, and segregated multiples thereof. The amount of active ingredient per dosage unit may range from 0.1 to 500 mg, particularly from 0.5 to 100 mg and preferably from 2 to 40 mg.

In view of the usefulness of the subject compounds and intermediates as immunostimulants, the present invention also provides a method of treating humans and warm-blooded animals suffering from disorders and/or diseases wherein the immune system is impaired, said method comprising administering to said humans or warm-blooded animals an effective immunostimulating amount of a compound of formula (I) or an intermediate of formula (II) or (VIII), a pharmaceutically acceptable acid addition salt thereof or a stereochemically isomeric form thereof, in admixture with a pharmaceutical carrier. Those of skill in treating subjects suffering from disorders and/or diseases wherein the immune system is impaired, could easily determine the effective immunostimulating amount of the compounds of formula (I) and the intermediates (II) and (VIII) from the test results presented hereinafter. In general it is contemplated that an effective daily dose of a compound of formula (I) or an intermediate of formula (II) or (VIII) would be from 0.01 mg/kg to 5 mg/kg body weight, preferably from 0.04 mg/kg to 2.5 mg/kg body weight per day. It may be appropriate to administer the required dose as a single dose or divided as two, three, four or more sub-doses at appropriate intervals throughout the day. Said sub-doses may be formulated as unit dosage forms. It is evident that said effective daily dose depends on the condition, the response of the treated subject, the severity of the disorder and/or disease and the evaluation of the physician prescribing the compounds of the instant invention, and that said effective amount may be lowered or increased accordingly. The effective amount ranges mentioned hereinabove are therefore guidelines only and are not intended to limit the scope nor the use of the present invention to any limit.

In a further aspect of the method according to the present invention there is also provided a method of treating patients suffering from neoplastic diseases, said method comprising the administration of an effective immunostimulating amount of a compound of formula (I) or an intermediate of formula (II) or (VIII) concomitant with antineoplastic therapy such as, for example, surgery, radiotherapy and in particular chemotherapy. As examples of antineoplastic drugs which may be used in chemotherapy according to the present method, there may be mentioned ancitabine (cycloxytidine), azathioprine, bleomycins, busulfan, calusterone, carboquone, cannustine, chlorambucil, cisplatin, cyclophosphamide, cytarabine, dacarbazine, dactinomycin, doxorubicin (adriamycin), dromostanolone propionate, epitiostanol (epithioadrostanol), estramustine phosphate, etoposide, fluorouracil, diethylstilbestrol diphosphate, hydroxyurea, lomustine, melengestrol, melphalan, 6-mercaptopurine, methotrexate, mitobronitol, mitomycin C, mitopodozide, mitotane, mycophenolic acid, nimustine, pipobroman, piposulfan, prednimustine, procarbazine, razoxane, tegafur, teniposide, testolactone, triethylenethiophosphoramide, thioguanine, triazequone, trophosphamide, uramustine, vinblastine, vincristine, vindesine and the like antirico-plastic drugs.

According to the present method an effective antineoplastic amount of an antineoplastic drug, in particular of one or more of the drugs specifically mentioned hereinabove, is administered to the subject to be treated, simultaneously, separately, or sequentially with an effective immunostimulating amount of a compound of formula (I) or an intermediate of formula (II) or (VIII). In general it is contemplated that an effective dose of the antineoplastic drug would be such as used commonly in antineoplastic therapy, and the effective immunostimulating amount of a compound of formula (I) or an intermediate of formula (II) or (VIII) would range from 0.01 mg/kg to 5 mg/kg body weight per day, preferably from 0.04 mg/kg to 2.5 mg/kg.

Said method further also comprises treating patients at risk of recurrent disease after having undergone antineoplastic therapy with an effective immunostimulating amount of a compound of formula (I) or an intermediate of formula (II) or (VIII).

The following examples are intended to illustrate and not to limit the scope of the present invention. Unless otherwise stated all parts therein are by weight.

Experimental Part

A. Preparation of the intermediates.

EXAMPLE 1 a) To a stirred solution of 21 parts of octadecanal in 65 parts of dichloromethane and 50 parts of 1,4-dioxane there were added dropwise 34.1 parts of bromine. After stirring for 4 hours at room temperature, the reaction mixture was poured into 250 parts of water. The product was extracted with dichloromethane and the extract was dried, filtered and evaporated, yielding 28 parts (95%) of 2-bromooctadecanal (interm. 1).

b) A mixture of 6.7 parts of thiourea, 28 parts of intermediate 1 and 80 parts of ethanol was stirred for 1 hour at reflux temperature. The reaction mixture was evaporated and the residue was washed with NaOH (aq.). The product was extracted with dichloromethane and the extract was dried, filtered and evaporated, yielding 11.8 parts (45%) of 5-hexadecyl-2-thiazolamine (interm. 2).

EXAMPLE 2

A mixture of 6 parts of 5-heptyl-2-thiazolamine (prepared as intermediate 2), 6 parts of 2-bromo-1-phenylethanone and 120 parts of acetonitrile was stirred overnight at room temperature. The precipitate was filtered off, washed with 2,2'-oxybispropane and dried, yielding 10 parts of 2-(5-heptyl-2,3-dihydro-2-imino-3-thiazolyl)-1-phenylethanone hydrobromide (interm. 3).

The intermediates listed in Tables 1 and 2 were prepared in a similar manner.

TABLE 1

| Interm. No. | $R^1$ | R | Physical data |
|---|---|---|---|
| 60 | $C_2H_5$ | 4-Br | mp. 150° C./HBr |
| 61 | $C_2H_5$ | H | mp. 178–179° C./HBr |
| 62 | $C_2H_5$ | 3,4-di(Cl) | mp. 169.8° C. (dec.)/HBr |
| 63 | $CH_3$ | H | mp. 169.3° C./HBr |
| 64 | $CH_3$ | 4-Br | mp. 269.5° C. (dec.)/HBr |
| 65 | $CH_3$ | 4-$CH_3O$ | mp. 201.6° C./HBr |
| 66 | $CH_3$ | 3-Br | mp. 204.3° C./HBr |
| 67 | $C_3H_7$ | H | HBr |
| 68 | $C_3H_7$ | 4-Cl | mp. 163.2° C./HBr |
| 69 | $C_3H_7$ | 3-Br | mp. 170° C./HBr |
| 70 | $CH_3$ | 4-I | mp. 230° C./HBr |
| 71 | $C_3H_7$ | 3-$NO_2$ | mp. 185–186° C./HBr |
| 72 | $CH_3$ | 3-$NO_2$ | mp. 212° C./HBr |
| 73 | $C_4H_9$ | H | mp. 148.9° C./HBr |
| 74 | $CH(CH_3)_2$ | H | mp. 188–189° C./HBr |
| 75 | $C_4H_9$ | 3-Br | mp. 158.4° C./HBr |
| 76 | $C_3H_7$ | 4-Br | mp. 169–170° C./HBr |
| 77 | $C_4H_9$ | 4-Br | mp. 160–163° C./HBr |
| 78 | $CH(CH_3)_2$ | 4-Br | mp. 185–187° C./HBr |
| 79 | $CH(CH_3)_2$ | 4-Cl | mp. 194–195° C./HBr |
| 80 | $CH(CH_3)_2$ | 4-$NO_2$ | mp. 230.1° C. (dec.)/HBr |
| 81 | $CH(CH_3)_2$ | 3-$NO_2$ | mp. 185° C. (dec.)/HBr |
| 82 | $C_6H_{13}$ | H | mp. 141.5° C./HBr |
| 83 | $C_6H_{13}$ | 4-Br | mp. 128.8° C./HBr |
| 84 | $C_3H_7$ | 4-$CH_3$ | mp. 152.8° C./HBr |
| 85 | $CH(CH_3)_2$ | 3-Br | mp. 181.4° C./HBr |
| 86 | $CH_3$ | 4-$CH_3$ | mp. 225.3° C./HBr |
| 87 | $C_6H_{13}$ | 3-Br | mp. 152.1° C./HBr |
| 88 | $C_5H_{11}$ | 3-Br | mp. 157.3° C./HBr |
| 89 | $C_5H_{11}$ | 4-Br | mp. 153.9° C./HBr |
| 90 | $C_5H_{11}$ | H | mp. 143.6° C./HBr |
| 91 | $C_2H_5$ | 4-$NO_2$ | HBr |
| 92 | $C_7H_{15}$ | H | HBr |
| 93 | $C_8H_{17}$ | H | mp. 150.7° C./HBr |
| 94 | $C_{10}H_{21}$ | H | HBr |
| 95 | $C_{16}H_{33}$ | H | HBr |
| 96 | $C_{11}H_{23}$ | H | HBr |
| 97 | $C_{12}H_{25}$ | H | HBr |
| 98 | $C_{18}H_{37}$ | H | HBr |
| 99 | $C_{13}H_{27}$ | H | HBr |
| 100 | $C_6H_{13}$ | 2-$CH_3$ | mp. 145.3° C./HBr |

TABLE 2

| Interm. No. | Ar | Physical data |
|---|---|---|
| 101 | 2-thienyl | mp. 192.0° C./HBr |
| 102 | 2-furanyl | mp. 162.3° C./HBr |
| 103 | 2-pyridinyl | HBr |
| 104 | 3-thienyl | mp. 149.0° C./HBr |
| 105 | 4-pyridinyl | HBr |
| 106 | 3-pyridinyl | HBr |

EXAMPLE 3

To a stirred and cooled (ice-bath) mixture of 10 parts of intermediate 3 in 120 parts of methanol them was added portionwise 1 part of sodium tetrahydroborate. After stirring for 2 hours at room temperature, the reaction mixture was diluted with 100 parts of water and the whole was evaporated. The residue was triturated in water, filtered off and dissolved in trichloromethane. This solution was dried, filtered and evaporated. The residue was crystallized from 2-propanol, yielding 5.3 parts of 5-heptyl-2,3-dihydro-2-imino-α-phenyl-3-thiazoleethanol; mp. 123.5° C. (interm. 4).

The intermediates listed in Tables 3 and 4 were prepared in a similar way.

TABLE 3

| Interm. no. | R | R¹ | R² | Physical data |
|---|---|---|---|---|
| 5 | 4-Cl | $CH_3$ | $CH_3$ | 152.2° C. |
| 6 | 4-Br | $C_2H_5$ | H | 166.1° C. |
| 7 | H | $CH_3$ | $CH_3$ | 140.5° C. |
| 8 | 4-Cl | $CH_3$ | $C_2H_5$ | 143.5° C. |
| 9 | 3-Br | $CH_3$ | $CH_3$ | 146.8° C. |
| 10 | 4-I | $CH_3$ | $CH_3$ | 156.7° C. |
| 11 | 4-Br | $CH_3$ | $CH_3$ | 146.5° C. |
| 12 | H | $C_2H_5$ | H | 146.4° C. |
| 13 | 3,4-$Cl_2$ | $C_2H_5$ | H | 138.7° C. |
| 14 | 4-Br | $CH_3$ | H | 162.7° C. |
| 15 | H | $CH_3$ | H | 141.3° C. |
| 16 | 3-Br | $CH_3$ | H | 146.3° C. |
| 17 | H | $C_3H_7$ | H | 137.2° C. |
| 18 | 3-Br | $C_3H_7$ | H | 122.8° C. |
| 19 | 4-I | $CH_3$ | H | 176.8° C. |
| 20 | 4-Cl | $C_3H_7$ | H | 162.9° C. |
| 21 | 3-$NO_2$ | $CH_3$ | H | 167.1° C. |
| 22 | 3-$NO_2$ | $C_3H_7$ | H | 94.5° C. |
| 23 | H | $C_4H_9$ | H | 125.7° C. |
| 24 | H | i-$C_3H_7$ | H | 148° C. |
| 25 | 3-Br | $C_4H_9$ | H | 95.8° C. |
| 26 | 4-Br | $C_4H_9$ | H | 170.5° C. |
| 27 | 3-$NO_2$ | i-$C_3H_7$ | H | 102.5° C. |
| 28 | 4-Br | i-$C_3H_7$ | H | 170.5° C. |
| 29 | 4-Br | $C_3H_7$ | H | 167.7° C. |
| 30 | 4-Br | $C_6H_{13}$ | H | 144.2° C. |
| 31 | 4-Cl | i-$C_3H_7$ | H | 183–185° C. |
| 32 | 3-Br | $C_6H_{13}$ | H | 87.6° C. |
| 33 | 3-Br | i-$C_3H_7$ | H | 119.1° C. |
| 34 | 3-Br | $C_5H_{11}$ | H | 73.7° C. |
| 35 | H | $C_5H_{11}$ | H | 124.9° C. |
| 36 | 4-Br | $C_5H_{11}$ | H | 159.1° C. |
| 37 | H | $C_6H_{13}$ | H | 118.5° C. |
| 38 | H | $C_8H_{17}$ | H | 120° C. |
| 39 | H | $C_{10}H_{21}$ | H | — |
| 40 | H | $C_{16}H_{33}$ | H | — |
| 41 | H | $C_{11}H_{23}$ | H | — |
| 42 | H | $C_{12}H_{25}$ | H | — |
| 43 | H | $C_{18}H_{37}$ | H | — |
| 44 | H | $C_{13}H_{27}$ | H | — |
| 45 | 4-Br | H | $CH_3$ | 141.6° C. |
| 46 | 3,4-$Cl_2$ | H | $CH_3$ | 161° C. |
| 47 | 4-$CH_3O$ | H | $CH_3$ | 129.7° C. |
| 48(*) | H | $C_{13}H_{27}$ | H | — |
| 49 | 2-$CH_3$ | $C_6H_{13}$ | H | 155.1° C./HBr |

(*)ethanol was used as solvent instead of methanol.

TABLE 4

| Interm. no. | R | R¹ | R² | Physical data |
|---|---|---|---|---|
| 50 | 2-thienyl | $C_6H_{13}$ | H | 193.5° C./HCl |
| 51 | 2-furyl | $C_6H_{13}$ | H | 135.8° C./HCl |
| 52 | 2-pyridyl | $C_6H_{13}$ | H | 242.9° C./2HBr |
| 53 | 3-thienyl | $C_6H_{13}$ | H | 183.8° C./HCl |
| 54 | 3-pyridyl | $C_6H_{13}$ | H | 186.0° C./2HCl |
| 55 | 4-pyridyl | $C_6H_{13}$ | H | 218.6° C./2HCl |

EXAMPLE 4 a) A mixture of 51 parts of 2-bromo-1-(2-thienyl)ethanone, 28.5 parts of 5-methyl-2-thiazolamine and 240 parts of acetonitrile was stirred for 1 hour while heating on a water-bath. After cooling, the precipitate was filtered off, washed with ethanol and dried in vacuo, yielding 54 parts of 2-(2,3-dihydro-2-imino-5-methyl-3-thiazolyl)-1 -(2-thienyl)ethanone hydrobromide; mp. 207.5°–208° C (interm. 56).

b) A mixture of 38 parts of intermediate 56, 19 parts of acetic anhydride, 19 parts of pyridine and 300 parts of trichloromethane was heated for 6 hours in a steam-bath. After cooling, the reaction mixture was washed with ammonium hydroxide. The organic layer was separated, dried, filtered and evaporated. The residue was recrystallized from methylbenzene, yielding 20 parts of N-[2,3-dihydro-3-[2-oxo-2-(2-thienyl)ethyl]-5-methyl-2-thiazolylidene]acetamide; mp. 187°–188.5° C. (interm. 57).

c) To a stirred suspension of 7 parts of intermediate 57 in 100 parts of methanol there were added dropwise 0.95 parts of sodium tetrahydroborate. After stirring for 1 hour at room temperature, the solvent was evaporated. The residue was taken up in water and extracted with trichloromethane. The extract was dried, filtered and evaporated. The residue was recrystallized from hot methylbenzene, yielding 6 parts of N-[2,3-dihydro-3-[2-hydroxy-2-(2-thienyl)ethyl]-5-methyl-2-thiazolylidene]acetamide; mp. 114°–115° C. (interm. 58).

In a similar manner there was also prepared N-[2,3-dihydro-3-[2-hydroxy-2-(2-thienyl)ethyl]-4-methyl-2-thiazolylidene]acetamide; mp. 105.5°–107° C. (interm. 59).

B. Preparation of the final compounds

EXAMPLE 5

A mixture of 4 parts of intermediate 4 and 36 parts of sulfuric acid was stirred for ½ hour at 0° C., and for 1½ hour at room temperature. The reaction mixture was poured into crushed ice and the whole was basified with NH₄OH (aq.). The product was extracted with dichloromethane and the extract was dried, filtered and evaporated. The residue was convened into the ethanedioate salt in 2-propanol. The product was filtered off and dried, yielding 3 parts of 2-heptyl-5,6-dihydro-6-phenylimidazo[2,1-b]thiazole ethanedioate; mp. 108.7° C. (comp. 34).

EXAMPLE 6

To a stirred solution of 9.8 parts of intermediate 6 in 75 parts of trichloromethane there were added dropwise 5 parts of thionyl chloride. After stirring for 1 hour at 50° C., the reaction mixture was evaporated and tile residue was taken up in 100 parts of Na₂CO₃ (aq.) 2N. This solution was stirred for 1 hour at 90° C., cooled and extracted with trichloromethane. The extract was dried, filtered and evaporated. The residue was crystallized from a mixture of methylbenzene and petroleumether, yielding 3.5 parts of 6-(4-bromophenyl)-2-ethyl-5,6-dihydroimidazo[2,1-b]thiazole; mp. 74.8° C. (comp. 2).

EXAMPLE 7

To a stirred and cooled (0° C.) amount of 16 parts of thionyl chloride there were added portionwise 5.5 parts of intermediate 58 while keeping the temperature below 10° C. After stirring for 2 hours at room temperature, there were added 50 parts of acetic anhydride at a temperature below 20° C. The formed acetylchloride was distilled off (136° C.) and the residue was evaporated. The residual oil was dissolved in a mixture of water and hydrochloric acid. After filtration, this solution was basified with NH₄OH and extracted with methylbenzene. The extract was dried, filtered and evaporated. The residue was convened into the ethanedioate salt in 2-propanol. The salt was filtered off, washed with 2-propanone and dried, yielding 1.5 parts of (±)-5,6-dihydro-2-methyl-6-(2-thienyl)imidazo[2,1-b]thiazole ethanedioate; mp. 170°–171.5° C. (comp. 56).

EXAMPLE 8

To a solution of 5.3 parts of (S)-(+)-2-mercapto-4-phenyl-2-imidazoline (U.S. Pat. No. 3,274,209) in 63 parts of acetic acid there were added 6.2 parts of 2-bromooctaldehyde. After stirring for 1½ hour at reflux temperature, the solvent was evaporated. The residue was taken up in water and the whole was basified with NH₄OH. The free base was extracted with methylbenzene and the extract was dried, filtered and evaporated. The residue was converted into the ethanedioate salt in 2-propanol. The salt was filtered off and dried, yielding 3.1 parts (27.4%) of product; mp. 132.7° C. The mother liquor was evaporated and the residue was treated with NH₄OH. The product was extracted with dichloromethane and the extract was dried, filtered and evaporated. The residue was purified by column chromatography (silica gel; CH₂Cl₂/CH₃OH (NH₃) 97.5:2.5). The eluent of the desired fraction was evaporated and the residue was converted into the ethanedioate salt as before, yielding 1.6 parts (14.2%) of product; mp. 136.3° C. Total yield: 4.7 parts (41.6%) of (S)-(−)-2-hexyl-5,6-dihydro-6-phenylimidazo[2,1-b]thiazole ethanedioate(1:1) (comp. 50). $[\alpha]_D^{20}$ (fraction 2)=−32.40°(conc.=1% in CH₃OH).

Compound 51 was prepared in a similar manner, using methanol as solvent instead of acetic acid and refluxing for 15 hours instead of 1½ hour.

Compound 52 was prepared similarly by first refluxing for 17 hours in methanol, then replacing the solvent by acetic acid and continuing reflux for 15 hours.

EXAMPLE 9

A mixture of 1.78 parts of 2-mercapto-4-phenyl-2-imidazoline, 44.5 parts of tetrahydrofuran and 0.92 parts of a dispersion of sodium hydride in mineral oil (50%) was stirred for 45 min. at room temperature. There were added 1.5 parts of 2-chlorocyclohexanone and stirring was continued for 2 hours. The reaction mixture was diluted with water and then evaporated. The residue was stirred in HCl 2N for 15 min and then the whole was basified with NH₄OH. The product was extracted with dichloromethane and the extract was dried, filtered and evaporated. The residue was purified twice by column chromatography (silica gel; CH₂Cl₂/CH₃OH 95:5; CH₂Cl₂/CH₃OH/CH₃OH(NH₃) 97:2:1). The eluent of the desired fraction was evaporated and the residue was converted into the ethanedioate salt in tetrahydrofuran. The salt was filtered off and dried, yielding 1.6 parts (46.2%) of 2,3,5,6,7,8-hexahydro-2-phenyl-imidazo[2,1-b]benzothiazole ethanedioate(1:1); mp. 146.2° C. (comp. 53).

EXAMPLE 10

3.8 parts of compound 33 were separated into the R and S isomers by preparative column chromatography (Chiracel OD®; hexanol/2-C₃H₇OH 90:10). The eluent of the (R)-(+) fraction was evaporated and the residue was converted into the ethanedioate salt in 2-propanol. The product was filtered off and dried, yielding 1.2 parts (24.0%) of (R)-(+)-2-hexyl-5,6-dihydro-6-phenylimidazo-[2,1-b]thiazole ethanedioate(1:1); mp. 135.1° C.; $[\alpha]_D^{20}$=+32.23° conc.=1% in CH₃OH) (comp. 54).

Evaporation of the eluent of the (S)-(−) fraction and similar treatment as for the (R)-(+) fraction yielded 1.1 parts (22.0%) of (S)-(−)-2-hexyl-5,6-dihydro-6-phenylimidazo[2,1-b]thiazole ethanedioate(1:1); mp. 142.2° C.; $[\alpha]_D^{20}$=32.34° (conc.=1% in CH₃OH) (comp. 50).

All the other compounds listed in Tables 5 and 6 were prepared following the procedure of the example referred to in the column Ex. No.

TABLE 5

| Comp. no. | Ex. no. | R | $R^1$ | $R^2$ | Physical data (mp. °C.) |
|---|---|---|---|---|---|
| 1 | 5 | 4-Cl | $CH_3$ | $CH_3$ | 154.4/$HNO_3$ |
| 2 | 6 | 4-Br | $C_2H_5$ | H | 74.8 |
| 3 | 5 | H | $CH_3$ | $CH_3$ | 157.3/$(COOH)_2$ |
| 4 | 5 | 4-Cl | $CH_3$ | $C_2H_5$ | 136.5/$HClO_4$ |
| 5 | 5 | 3-Br | $CH_3$ | $CH_3$ | 161.8/$(COOH)_2$ |
| 6 | 6 | 4-I | $CH_3$ | $CH_3$ | 228.2/$HClO_4$ |
| 7 | 5 | 4-Br | $CH_3$ | $CH_3$ | 154.5/$(COOH)_2$ |
| 8 | 5 | H | $C_2H_5$ | H | 164 (dec.)/$(COOH)_2$ |
| 9 | 5 | 3,4-$Cl_2$ | $C_2H_5$ | H | 148.2/$(COOH)_2$ |
| 10 | 5 | H | $CH_3$ | H | 82.8 |
| 11 | 5 | 4-Br | $CH_3$ | H | 178.5/$(COOH)_2$ |
| 12 | 5 | 3-Br | $CH_3$ | H | 142/cyclohexanesulfamate |
| 13 | 5 | H | $C_3H_7$ | H | 156.5/cyclohexanesulfamate |
| 14 | 5 | 3-Br | $C_3H_7$ | H | 146–147/cyclohexanesulfamate |
| 15 | 6 | 4-I | $CH_3$ | H | 190.9/$(COOH)_2$ |
| 16 | 5 | 4-Cl | $C_3H_7$ | H | 138.6/$(COOH)_2$ |
| 17 | 5 | 3-$NO_2$ | $CH_3$ | H | 205.9/HCl |
| 18 | 5 | 3-$NO_2$ | $C_3H_7$ | H | 204–205.3/HCl |
| 19 | 5 | H | $C_4H_9$ | H | 161.8/cyclohexanesulfamate |
| 20 | 5 | H | i-$C_3H_7$ | H | 174.2/$(COOH)_2$ |
| 21 | 5 | 3-Br | $C_4H_9$ | H | 189/HCl |
| 22 | 5 | 4-Br | $C_4H_9$ | H | 210.4/HCl |
| 23 | 5 | 3-$NO_2$ | i-$C_3H_7$ | H | 205 (dec.)/cyclohexanesulfamate |
| 24 | 5 | 4-Br | i-$C_3H_7$ | H | 207.7/HCl |
| 25 | 5 | 4-Br | $C_3H_7$ | H | 166.1/$(COOH)_2$ |
| 26 | 5 | 4-Br | $C_6H_{13}$ | H | 132.3/$(COOH)_2$ |
| 27 | 5 | 4-Cl | i-$C_3H_7$ | H | 167.8/$(COOH)_2$ |
| 28 | 5 | 3-Br | $C_6H_{13}$ | H | 188.3/HCl |
| 29 | 5 | 3-Br | i-$C_3H_7$ | H | 217 (dec.)/HCl |
| 30 | 5 | 3-Br | $C_5H_{11}$ | H | 189.5–192/HCl |
| 31 | 5 | 4-Br | $C_5H_{11}$ | H | 210.6/HCl |
| 32 | 5 | H | $C_5H_{11}$ | H | 110.5/$(COOH)_2$ |
| 33 | 5 | H | $C_6H_{13}$ | H | 110.1/$(COOH)_2$ |
| 34 | 5 | H | $C_7H_{15}$ | H | 108.7/$(COOH)_2$ |
| 35 | 5 | H | $C_8H_{17}$ | H | 149.2 (dec.)/HCl |
| 36 | 5 | H | $C_{10}H_{21}$ | H | 152.4/HCl |
| 37 | 5 | H | $C_{16}H_{33}$ | H | 149.7/HCl |
| 38 | 5 | H | $C_{11}H_{23}$ | H | 143.8/HCl |
| 39 | 5 | H | $C_4H_9$ | H | 150.1/HCl |
| 40 | 5 | H | $C_{12}H_{25}$ | H | 149.4/HCl |
| 41 | 5 | H | $C_{18}H_{37}$ | H | 149.1/HCl |
| 42 | 5 | H | $C_{13}H_{27}$ | H | 146.1/HCl |
| 43 | 5 | 4-Br | H | $CH_3$ | 167.4/$(COOH)_2$ |
| 44 | 5 | H | H | $CH_3$ | 186.3/$(COOH)_2$ |
| 45 | 5 | 3,4-$Cl_2$ | H | $CH_3$ | 170.3/$(COOH)_2$ |
| 46 | 6 | 4-$CH_3O$ | H | $CH_3$ | 175.7/$(COOH)_2$ |
| 47 | 6 | 2-$CH_3$ | $C_6H_{13}$ | H | 106.0/$(COOH)_2$ |
| 48 | 8 | H | $C_6H_5$ | H | 216.1/$(COOH)_2$ |
| 49 | 8 | H | c.$C_6H_{11}$-$CH_2$ | H | 150.4/$(COOH)_2$ |
| 50 | 8 or 10 | H | $C_6H_{13}$ | H | 136.3/$(COOH)_2$ /(S)-(−) $[\alpha]_{D\ 1\%MeOH}^{20} = -32.40°$ |
| 51 | 8 | H | H | $C_6H_{13}$ | 124.1/$(COOH)_2$ |
| 52 | 8 | H | c.$C_6H_{11}$ | H | 188.1/$(COOH)_2$ |
| 53 | 9 | H | −$(CH_2)_4$− | | 146.2/$(COOH)_2$ |
| 54 | 10 | H | $C_6H_{13}$ | H | 135.1/$(COOH)_2$/(R)-(+) $[\alpha]_{D\ 1\%MeOH}^{20} = +32.23°$ |

TABLE 6

| Co. No. | Ex. No. | Ar | R¹ | R² | physical data (mp. °C.) |
|---|---|---|---|---|---|
| 55 | 7 |  | H | CH₃ | 182.5–184/(COOH)₂ |
| 56 | 7 |  | CH₃ | H | 170–171.5/(COOH)₂ |
| 57 | 6 |  | C₆H₁₃ | H | 122.6/(COOH)₂ |
| 58 | 6 |  | C₆H₁₃ | H | 114.4/(COOH)₂ |
| 59 | 6 |  | C₆H₁₃ | H | 116.1/3/2(COOH)₂ |
| 60 | 6 |  | C₆H₁₃ | H | 105.5/(COOH)₂ |
| 61 | 6 |  | C₆H₁₃ | H | 79.2/2(COOH)₂ |
| 62 | 6 |  | C₆H₁₃ | H | 156.4/3(COOH)₂ |
| 63 | 6 | C₆H₅ | C₆H₁₃ | H | mp. 150.7° C./* |
| 64 | 10 | C₆H₅ | C₆H₁₃ | H | 152.7° C./(+)-(R)/* |
| 65 | 10 | C₆H₅ | C₆H₁₃ | H | 152.4° C./(−)-(S)/* |

*: cyclohexylsulfamate

C. Pharmacological example

The immunostimulating properties of the present compounds can be demonstrated in the following test procedures.

EXAMPLE 11

Costimulating effect on ³H-thymidine incorporation in murine thymocytes stimulated by Concanavalin A. (described in Int. J. Immunopharm., 1, 233–237 (1979).

The culture medium consisted of Earle's minimal essential medium (MEM) supplemented with 100 U/ml penicillin, 100 μg/ml streptomycin and 2 mM L-glutamine (GIBCO, Grand Island, N.Y.), together with 5% fetal calf serum (FCS).

Culture procedure

Mouse thymuses were aseptically removed, teased with forceps in cold culture medium and filtered through a nylon gauze. The cells were then washed twice with medium. Cell counts and viability testing were carded out in a Neubauer hemocytometer. Cultures were done in triplicate in 16×25 mm loosely capped plastic tubes (Falcon no. 3033) Cultures contained 10⁶ viable thymocytes, Con A (2 μg) and test compound in a total volume of 1.0 ml. The tubes were incubated at 37° C. in a 5% CO₂ atmosphere. After incubation for 64 h, the cells were pulsed for 4 h by adding 1 μCi of ³H-thymidine. After this time cultures were processed by washing once with 2 ml 0.9% NaCl and twice with 1 ml 5% trichloroacetic acid. The resulting precipitate was dissolved in 0.3 ml 0.5N sodium hydroxide, transferred to counting vials and 10 ml Instagel was added. Incorporation was measured using a Packard Tri-Carb liquid scintillation spectrometer.

The costimulation effect of the tested compounds was determined as follows. For different concentrations ($10^{-4}$ down to $10^{-10}$M, in tenfold dilutions) of the test compound of formula (I), there was calculated the ratio between the number of cpm/culture in the presence of Concanavalin A (2 μg/ml) and test compound, and the number of cpm/culture in the presence of Concanavalin A (2 μg/ml) alone. Table 7 shows the concentration (M) of test compound at which maximal costimulation effects (i.e. maximum calculated ratio) on ³H-thymidine incorporation were observed.

TABLE 7

| Comp. No. | Max. costimulation effect (M) |
|---|---|
| 18 | $10^{-6}$ |
| 20 | $5 \cdot 10^{-6}$ |
| 21 | $10^{-6}$ |
| 22 | $10^{-6}$ |
| 23 | $10^{-6}$ |
| 25 | $10^{-6}$ |
| 26 | $10^{-7}$ |
| 30 | $5 \cdot 10^{-7}$ |
| 31 | $10^{-7}$ |
| 32 | $10^{-7}$ |
| 33 | $10^{-7}$ |
| 34 | $10^{-7}$ |
| 35 | $10^{-7}$ |
| 36 | $10^{-6}$ |
| 37 | $10^{-6}$ |
| 39 | $10^{-6}$ |

Reference compound: levamisole: $10^{-4}$ M

EXAMPLE 12

Costimulating effect on ³H-thymidine incorporation in murine splenocytes stimulated by anti-CD3

The culture medium consisted of RPMI supplemented with 100 U/ml penicillin, 100 μg/ml streptomycin and 2 mM L-glutamine (GIBCO, Grand Island, N.Y.), together with 5% fetal calf serum (FCS).

Culture procedure

Mouse spleens were aseptically removed, teased with forceps in cold culture medium and filtered through a nylon gauze. The cells were then washed twice with medium. Cell counts and viability testing were carried out in a Neubauer hemocytometer. Cultures were done in triplicate in 16×25 mm loosely capped plastic tubes (Falcon no. 3033). Cultures contained 2.10⁵ viable splenocytes, anti-CD3 (0.1 μg) and test compound in a total volume of 0.2 ml. The tubes were incubated at 37° C. in a 5% CO₂ atmosphere. After incubation for 64 h, the cells were pulsed for 4 h by adding 1 μCi of ³H-thymidine. After this time cultures were processed by washing once with 2 ml 0.9% NaCl and twice with 1 ml 5% trichloroacetic acid. The resulting precipitate was dissolved in 0.3 ml 0.5N sodium hydroxide, transferred to counting vials and 10 ml Instagel was added. Incorporation was measured using a Packard Tri-Carb liquid scintillation spectrometer.

The costimulation effect of the tested compounds was determined as follows. For different concentrations ($10^{-4}$ down to $10^{-10}$M, in tenfold dilutions) of the test compound of formula (I) or of the test intermediate of formula (II) or (VIII), there was calculated the ratio between the number of cpm/culture in the presence of anti-CD3 (0.5 µg/ml) and test compound, and the number of cpm/culture in the presence of anti-CD3 (0.5 µg/ml) alone. Tables 8 and 9 show the concentration (M) of test compound of formula (I) or of the test intermediate of formula (II) or (VIII) at which maximum costimulation effects (i.e. maximum calculated ratio) on $^3$H-thymidine incorporation was observed. Below table 8 the test result for a number of compounds known from GB-1,043,489 are given.

TABLE 8

| Comp. No. | Max. Costimulation effect (M) |
|---|---|
| 57 | $10^{-6}$ |
| 59 | $10^{-7}$ |
| 60 | $10^{-7}$ |
| 61 | $10^{-7}$ |
| 62 | $10^{-7}$ |
| 63 | $10^{-8}$ |
| 64 | $10^{-8}$ |
| 65 | $10^{-7}$ |

Reference compound:levamisole:$10^{-4}$ M

| GB-1,043,489 | Maximum Costimulation effect at |
|---|---|
| [structure: thiophene-CH-imidazoline-thiazole] | $10^{-4}$ M |
| [structure: phenyl-CH-imidazoline-thiazole] | $10^{-4}$ M |
| [structure: nitro-phenyl-CH-imidazoline-thiazole] | $10^{-5}$ M |
| [structure: bromo-phenyl-CH-imidazoline-thiazole] | $10^{-5}$ M |

TABLE 9

| Interm No. | Max. Costimulation effect (M) |
|---|---|
| 37 | $10^{-6}$ |
| 38 | $10^{-6}$ |
| 51 | $10^{-6}$ |
| 52 | $10^{-6}$ |
| 53 | $10^{-6}$ |
| 54 | $10^{-6}$ |
| 55 | $10^{-6}$ |
| 82 | $10^{-6}$ |
| 93 | $10^{-6}$ |
| 101 | $10^{-6}$ |
| 102 | $10^{-6}$ |
| 104 | $10^{-6}$ |

D. Composition Examples.

The following formulations exemplify typical pharmaceutical compositions in dosage unit form suitable for systemic administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

EXAMPLE 13

Oral drops 500 g of the A.I. is dissolved in 0.5 l of 2-hydroxypropanoic acid and 1.5 l of the polyethylene glycol at 60°–80° C. After cooling to 30°–40°~ C. there are added 35 l of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50 l, providing an oral drop solution comprising 10 mg/ml of the A.I. The resulting solution is filled into suitable containers.

EXAMPLE 14

Oral solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE 15

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 16

Film-coated tablets
Preparation of the tablet core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90®) in about 200 ml of water. The wet powder mixture is sieved, dried and sieved again. Then there are added 100 g microcrystalline cellulose (Avicel®) and 15 g hydrogenated vegetable oil (Sterorex®). The whole is mixed well and compressed into tablets, giving 10.000 tablets, each comprising 10 mg of the active ingredient.

Coating

To a solution of 10 g methyl cellulose (Methocel 60 HG®) in 75 ml of denaturated ethanol there is added a solution of 5 g of ethyl cellulose (Ethocel 22 cps®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109®) and the whole is homogenated. The tablet cores are coated with the thus obtained mixture in a coating apparatus.

EXAMPLE 17

Injectable solutions 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 4 g of the A.I. The solution is cooled to room temperature and supplemented with water for injection q.s. ad 1 l volume, giving a solution of 4 mg A.I. per ml. The solution is sterilized by filtration (U.S.P. XVII p. 811) and filled in sterile containers.

EXAMPLE 18

Suppositories 3 g A.I. is dissolved in a solution of 3 g 2,3-dihydroxybutanedioic acid in 25 ml polyethylene glycol 400. 12 g surfactant (SPAN®) and triglycerides (Witepsol 555®) q.s. ad 300 g are molten together. The latter mixture is mixed well with the former solution. The thus obtained mixture is poured into moulds at a temperature of 37°–38° C. to form 100 suppositories each containing 30 mg of the A.I.

We claim:

1. A compound of the formula:

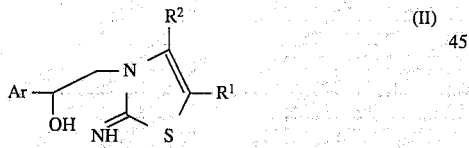

(II)

a pharmaceutically acceptable acid addition salt thereof or a stereochemically isomeric form thereof, wherein:

Ar is phenyl optionally substituted with from 1 to 3 substituents each independently selected from halo, hydroxy, $C_{1-6}$alkyloxy, mercapto, $C_{1-6}$alkylthio, $C_{1-6}$alkyl, nitro, amino, mono- and di($C_{1-6}$alkyl)amino, $C_{1-6}$alkylcarbonylamino, arylcarbonylamino, $C_{1-6}$alkylsulfonylamino, trifluoromethyl, cyano, aminocarbonyl, mono- and di($C_{1-6}$alkyl)aminocarbonyl, hydroxycarbonyl, $C_{1-6}$alkyloxycarbonyl, carboxaldehyde and hydroxymethyl; pyridinyl; thienyl, furanyl or furanyl substituted with $C_{1-6}$alkyl or halo;

$R^1$ is $C_{3-10}$alkyl, ($C_{3-7}$cycloalkyl)$C_{1-6}$alkyl, $C_{3-7}$cycloalkyl, aryl or (aryl)$C_{1-6}$alkyl;

$R^2$ is hydrogen, $C_{1-20}$alkyl, ($C_{3-7}$cycloalkyl)$C_{1-6}$alkyl, $C_{3-7}$cycloalkyl, aryl or (aryl)$C_{1-6}$alkyl;

or $R^1$ and $R^2$ together may form a $C_{3-6}$alkandiyl radical;

wherein in the foregoing each aryl independently is phenyl optionally substituted with from 1 to 3 substituents each independently selected from halo, hydroxy, $C_{1-6}$alkyloxy, $C_{1-6}$alkyl, nitro, amino, trifluoromethyl or cyano.

2. A compound according to claim 1 wherein $R^1$ is $C_{4-10}$alkyl and Ar is phenyl optionally substituted with one halo, nitro, methoxy or methyl.

3. A compound according to claim 1 wherein $R^2$ is hydrogen; and Ar is pyridinyl; thienyl; or phenyl optionally substituted with halo, nitro, $C_{1-4}$alkyloxy of $C_{1-4}$alkyl.

4. A compound according to claim 3 wherein $R^1$ is $C_{4-10}$alkyl and Ar is phenyl optionally substituted with one halo, nitro, methoxy or methyl.

5. A compound according to claim 1 wherein said compound is 5-hexyl-2,3-dihydro-2-imino-α-phenyl-3-thiazoleethanol.

6. A compound of the formula:

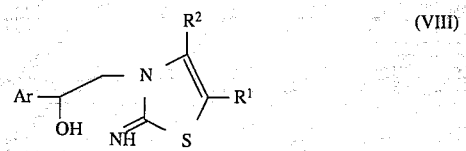

(VIII)

a pharmaceutically acceptable acid addition salt thereof or a stereochemically isomeric form thereof, wherein:

Ar is phenyl optionally substituted with halo, nitro, $C_{1-4}$alkyloxy or $C_{1-4}$alkyl; pyridinyl; or thienyl;

$R^1$ is $C_{3-10}$alkyl, ($C_{3-7}$cycloalkyl)$C_{1-6}$alkyl, $C_{3-7}$cycloalkyl, or aryl; and $R^2$ is hydrogen;

wherein in the foregoing aryl is phenyl optionally substituted with from 1 to 3 substituents each independently selected from halo, hydroxy, $C_{1-6}$alkyloxy, $C_{1-6}$alkyl, nitro, amino, trifluoromethyl or cyano.

7. A compound according to claim 6 wherein $R^1$ is $C_{4-10}$alkyl and Ar is phenyl optionally substituted with one halo, nitro, methoxy or methyl.

8. A compound according to claim 6 wherein said compound is 2-(5-hexyl-2,3-dihydro-2-imino-3-thiazolyl)-1-phenylethanone.

9. A compound of the formula:

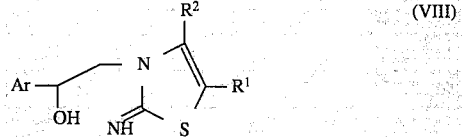

(VIII)

a pharmaceutically acceptable acid addition salt thereof or a stereochemically isomeric form thereof, wherein:

Ar is phenyl optionally substituted with 1 substituent selected from the group consisting of bromo, chloro, iodo, nitro, methoxy and methyl;

$R^1$ is $C_{4-10}$alkyl;

$R^2$ is hydrogen, $C_{1-20}$alkyl, ($C_{3-7}$cycloalkyl)$C_{1-6}$alkyl, $C_{3-7}$cycloalkyl or (aryl)$C_{1-6}$alkyl;

wherein in the foregoing aryl is phenyl optionally substituted with from 1 to 3 substituents each independently selected from halo, hydroxy, $C_{1-6}$alkyloxy, $C_{1-6}$alkyl, nitro, amino, trifluoromethyl or cyano.

* * * * *